US011020085B2

(12) United States Patent
Clark (10) Patent No.: US 11,020,085 B2
(45) Date of Patent: Jun. 1, 2021

(54) SPECTRAL DOPPLER PROCESSING WITH ADAPTIVE SAMPLE WINDOW SIZE (71) Applicant: KONINKLIJKE PHILIPS N.V., Eindhoven (NL)

(72) Inventor: David Wesley Clark, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 372 days.

(21) Appl. No.: 15/755,603

(22) PCT Filed: Aug. 18, 2016

(86) PCT No.: PCT/IB2016/054942
§ 371 (c)(1),
(2) Date: Feb. 27, 2018

(87) PCT Pub. No.: WO2017/033098
PCT Pub. Date: Mar. 2, 2017

(65) Prior Publication Data
US 2019/0021691 A1 Jan. 24, 2019

Related U.S. Application Data (60) Provisional application No. 62/210,518, filed on Aug. 27, 2015.

(51) Int. Cl.
A61B 8/06 (2006.01)
A61B 8/00 (2006.01)
(Continued)

(52) U.S. Cl.
CPC ............. A61B 8/06 (2013.01); A61B 8/463 (2013.01); A61B 8/488 (2013.01); G01S 7/5208 (2013.01);
(Continued)

(58) Field of Classification Search
CPC . G01S 7/5208; G01S 15/8915; G01S 15/8979
See application file for complete search history.

(56) References Cited

U.S. PATENT DOCUMENTS 5,379,770 A    1/1995   Van Veen
5,634,465 A *   6/1997   Schmiesing ............ G01S 15/58
                                                  600/454
(Continued)

FOREIGN PATENT DOCUMENTS

EP     2180339 A1   4/2010
JP     06319735 A   11/1994
(Continued)

OTHER PUBLICATIONS

Bracic et al. "Wavelet-based Analysis of Human Blood-flow Dynamics". Bulletin of Mathematical Biology (1998) 60, 919-935. Article No. bu980047. (Year: 1998).*

(Continued)

Primary Examiner — Serkan Akar
Assistant Examiner — Jillian K. McGough (57) ABSTRACT A spectral Doppler processor for an ultrasound system produces blood flow velocity estimates by processing a sequence of complex blood flow echo samples with an FFT algorithm. The FFT algorithm is executed with a long window of samples to produce velocity estimates with good velocity precision and is executed with a short window of samples to produce velocity estimates with good time precision. The long window algorithm is used when blood flow velocity is not changing rapidly, and the short window algorithm is used when blood flow velocity is changing rapidly.

13 Claims, 4 Drawing Sheets (51) Int. Cl.
   *A61B 8/08*   (2006.01)
   *G01S 15/89*  (2006.01)
   *G01S 7/52*   (2006.01)

(52) U.S. Cl.
   CPC ...... *G01S 15/8915* (2013.01); *G01S 15/8979* (2013.01)

(56) References Cited

U.S. PATENT DOCUMENTS

| | | | |
|---|---|---|---|
| 6,491,636 B2 | 12/2002 | Chenal et al. | |
| 6,733,454 B1* | 5/2004 | Bakircioglu | A61B 8/06 600/453 |
| 7,537,568 B2 | 5/2009 | Moehring | |
| 8,055,075 B1* | 11/2011 | Tamura | G06T 5/003 382/199 |
| 8,200,028 B2* | 6/2012 | Gabso | H04N 19/14 382/232 |
| 2005/0137479 A1* | 6/2005 | Haider | A61B 8/06 600/440 |
| 2006/0020203 A1* | 1/2006 | Tamura | G06T 5/20 600/437 |
| 2007/0167790 A1 | 7/2007 | Kim et al. | |
| 2007/0293759 A1* | 12/2007 | Eilers | A61B 8/06 600/454 |
| 2008/0015440 A1 | 1/2008 | Shandas et al. | |
| 2009/0149759 A1* | 6/2009 | Baba | A61B 8/483 600/454 |
| 2010/0099990 A1* | 4/2010 | Lee | A61B 8/06 600/453 |
| 2010/0286523 A1 | 11/2010 | Kim et al. | |
| 2013/0172749 A1 | 7/2013 | Lee et al. | |
| 2014/0221838 A1 | 8/2014 | Loupas et al. | |
| 2015/0331103 A1* | 11/2015 | Jensen | G01S 15/8984 367/7 |

FOREIGN PATENT DOCUMENTS

| | | |
|---|---|---|
| JP | 04031116 B2 | 1/2008 |
| JP | 2008043495 A | 2/2008 |
| KR | 1117838 B1 | 3/2012 |
| WO | 2007023438 A2 | 3/2007 |
| WO | 2014083373 A1 | 6/2014 |

OTHER PUBLICATIONS

Kanade et al "A Stereo Matching Algorithm With an Adaptive Window: Theory and Experiment" IEEE Transactions on Pattern Analysis and Machine Intelligence, vol. 16, No. 9, Sep. 1994 p. 920-932.

* cited by examiner

SPECTRAL DOPPLER PROCESSING WITH ADAPTIVE SAMPLE WINDOW SIZE

This application is the U.S. National Phase application under 35 U.S.C. § 371 of International Application No. PCT/M2016/054942, filed on Aug. 18, 2016, which claims the benefit of Provisional Application Ser. No. 62/210,518, filed Aug. 27, 2015. These applications are hereby incorporated by reference herein.

This invention relates to medical diagnostic systems and, in particular, to diagnostic ultrasound systems for assessing blood flow with spectral Doppler analysis.

A significant procedure in many standard vascular ultrasound exams is to obtain an assessment of a stenosis, or narrowing, of an artery. This is typically assessed using the ultrasound system's Color Doppler mode to find the stenosis and the spectral Doppler mode at the location of a suspected stenosis to measure the peak flow velocity, which correlates with the degree of stenosis. Medical ultrasound imaging systems have a spectral Doppler mode to display a spectrogram of blood velocity vs. time for a small region of interest, referred to as a sample volume. The mode can use either continuous wave (CW) or pulsed wave (PW) transmission to acquire a stream of echo samples from the sample volume which are processed to produce the spectrogram. In the spectrogram display, the horizontal axis is time, the vertical axis is velocity (Doppler frequency), and the brightness represents signal power. The processing typically uses Fast Fourier Transforms (FFTs) of overlapping time windows of the demodulated data stream of samples, with smoothly tapered window shapes such as Hann or Hamming to reduce frequency sidelobes.

The rate at which the processed samples are acquired will affect the accuracy of the resultant spectrogram. This acquisition rate can vary due to numerous factors, such as the depth of the sample volume in the body and multiplexing of spectral Doppler sample acquisition with the acquisition of echoes for other modes, such as samples for a B mode display of the anatomy or color Doppler data. Particularly for PW Doppler, where the sample rate is often relatively slow, the FFT window length, the number of successive samples which are processed by the FFT velocity estimation algorithm, has a very significant effect on the velocity and time resolution. Long windows of many samples produce a spectrogram with good velocity resolution but blurred in time, while short windows of fewer samples produce a spectrogram with good time resolution but blurred in velocity. A relatively short window is the typical aesthetic preference. The maximum velocity outline of the signal spectrum is often interpreted as representing the blood motion, and quantitative peak velocity measurements are often the primary use for spectral Doppler mode. The short FFT window can cause a significant velocity over-estimation bias. Accordingly it is desirable to use an FFT window length which is better adapted to produce both good time resolution and good velocity resolution.

In some aspects, the present invention includes ultrasonic diagnostic imaging systems with a spectral Doppler display mode. The systems can include a source of complex echo data samples returned from a location of blood flow, a first spectrogram processor configured to execute an FFT algorithm using a window of a first number of complex echo data samples and produces velocity estimates, a second spectrogram processor configured to execute an FFT algorithm using a window of a second number of complex echo data samples and produces velocity estimates, and a select/interpolate processor responsive to the velocity estimates from the first and second spectrogram processors and configured to produce an adaptive Doppler velocity spectrogram.

In certain aspects, the systems can include an edge detector, having inputs coupled to the spectrogram processors and an output coupled to the select/interpolate processor which can produce an adaptive Doppler velocity spectrogram in response to the output of the edge detector. The select/interpolate processor can be further operative to produce an adaptive Doppler velocity spectrogram by interpolating spectrograms produced by the first and second spectrogram processors. The edge detector can include a horizontal edge detector having an input coupled to the first spectrogram processor and a vertical edge detector having an input coupled to the second spectrogram processor, and the first number of complex echo data samples is greater than the second number of complex echo data samples. In some aspects, the select/interpolate processor is responsive to detection of a horizontal spectral segment edge by the horizontal edge detector and configured to select a spectrogram produced by the first spectrogram processor as an adaptive velocity Doppler spectrogram. The select/interpolate processor can also be responsive to detection of a vertical spectral segment edge by the vertical edge detector and configured to select a spectrogram produced by the second spectrogram processor as an adaptive velocity Doppler spectrogram.

In some aspects, the source of complex echo data samples further comprises a source of complex echo data samples acquired in a CW Doppler mode and/or in a PW Doppler mode. In certain aspects, the complex echo data samples further comprise a sequence of time-sequential complex echo data samples.

In certain aspects, the systems can include a third spectrogram processor configured to execute an FFT algorithm using a window of a third number of complex echo data samples and to produce velocity estimates. In some cases, the first number is greater than the second number and the second number is greater than the third number.

In some aspects, the select/interpolate processor utilizes velocity estimates produced by the first spectrogram processor to produce an adaptive velocity spectrogram with good velocity precision. The select/interpolate processor can also use velocity estimates produced by the third spectrogram processor to produce an adaptive velocity spectrogram with good time precision. The select/interpolate processor can use velocity estimates produced by the second spectrogram processor to produce an adaptive velocity spectrogram with average velocity and time precision. The select/interpolate processor can use velocity estimates produced by the third spectrogram processor in response to the detection of a vertical spectral segment edge and/or the detection of a horizontal spectral segment edge.

In certain aspects, the present invention includes ultrasound systems having instructions thereon, which when executed, cause the system to perform the following steps: receive complex echo data samples returned from a location of blood flow; execute an FFT algorithm using a window of a first number of complex echo data samples and produce first velocity estimates; execute an FFT algorithm using a window of a second number of complex echo data samples and produce second velocity estimates; and based on the first and second velocity estimates, produce an adaptive Doppler velocity spectrogram. In some aspects, the instructions can further cause the system to produce the adaptive Doppler velocity spectrogram based on the output of an edge detector, and/or produce the adaptive Doppler velocity spectrogram by interpolating spectrograms from first and second spectrogram processors.

In some aspects, the instructions can cause the system to execute an FFT algorithm using a window of a third number of complex echo data samples and to produce third velocity estimates, where the first number is greater than the second number and the second number is greater than the third number.

In accordance with the principles of the present invention, diagnostic ultrasound systems and methods are described in which the FFT window size is adapted to the present character of the spectrogram. In an illustrated implementation, the demodulated sample data stream is processed with multiple FFT window sizes in parallel to construct multiple spectrograms for analysis. Two-dimensional spatial filters that approximate a derivative operator in one direction but are otherwise smoothing, are applied to the spectrograms. Filters can be carried out through programming interconnects (e.g. signal connections) within a section of a field-programmable gate array (FPGA) that implements one or more filters for the received signals. Longer window spectrograms are filtered to detect horizontal signal edges, and the shorter window spectrograms are filtered to detect vertical signal edges. The character of the detected horizontal and vertical edges guides the selection or interpolation from the multiple spectrograms at each horizontal and vertical display location (pixel) to construct an adaptively combined spectrogram. Alternatively, the data could be processed using variable window lengths. The adaptive spectrogram uses long time windows for good velocity resolution in time periods where the signal velocity is changing slowly, e.g., diastole, and short time windows for good time resolution in time periods where the signal velocity is changing rapidly, e.g., systole. The result is a spectrogram with good time precision when the blood flow velocity is changing rapidly, and good velocity precision when the blood flow velocity is changing slowly.

Figure 1:
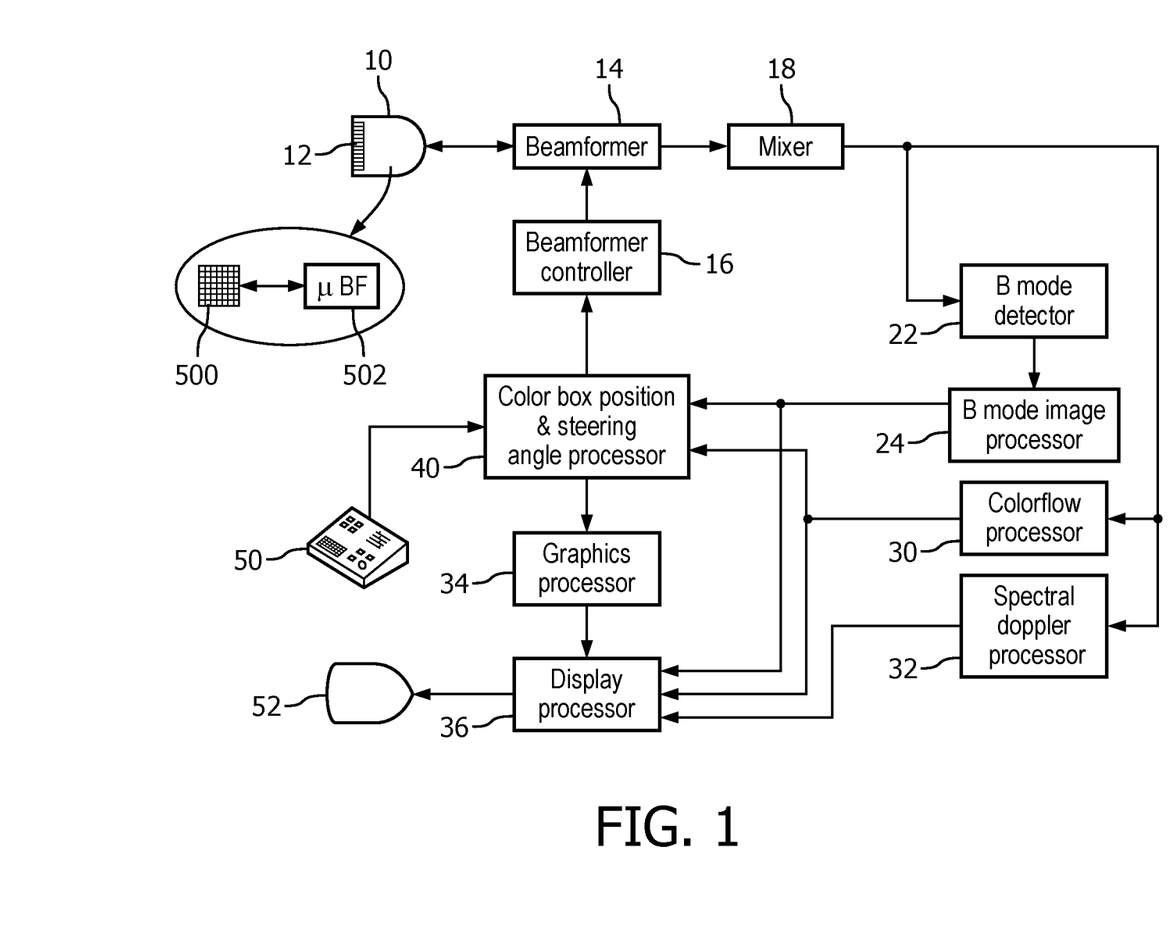
FIG. 1 illustrates in block diagram form an ultrasonic diagnostic imaging system constructed in accordance with the present invention.

Referring first to FIG. 1, an ultrasound system constructed in accordance with the principles of the present invention is shown in block diagram form. An ultrasound probe 10 contains an array 12 of transducer elements which transmit ultrasound waves into the body and receive returning echo signals. The transmitted waves are directed in beams or scanlines to interrogate a region of interest in the body. A one-dimensional array can be used to transmit beams over a single plane for two dimensional imaging. Alternatively, the probe 10 is a matrix array probe having a two-dimensional array of transducer elements 500 coupled to a probe microbeamformer 502. A matrix array probe can be used to transmit beams over a single scan plane or over a volumetric region of the body for three dimensional imaging. The beams can be steered and focused in different directions by the probe to interrogate tissue in specific locations or blood flow in specific directions. Control and processing of beams on transmit and receive is provided by a beamformer controller 16, which controls the microbeamformer 502 and a system beamformer 14 to transmit properly formed beams and beamform the received signals through delay and summation into coherent echo signals. In a two-stage beamforming system as shown in FIG. 1, partial beamforming of received signals is performed by the microbeamformer 502 and completion of the beamforming process is performed by the system beamformer 14. The beamformers can control the transducer array to scan beams over a desired image plane, for example, and to repetitively scan beams over an area of the image plane in which blood flow is to be assessed at a pulse repetition frequency (PRF, the sampling rate) appropriate for the velocities of blood flow present in that region of the body.

A mixer (or QBP filter) 18 demodulates the echo signals into baseband quadrature I and Q components. Alternatively, a quadrature bandpass filter may be used. A B mode detector 22 uses the I and Q components to perform B mode detection for tissues images by taking the square root of the sum of the squares of the I and Q components. The detected echo intensities are processed by a B mode image processor 24 on a spatial basis to form a two or three dimensional image of the tissue in the body, which is processed for display by display processor 36 and displayed on display screen 52. Processors described herein, such as the spectrogram processors and the select/interpolate processor, can include one or more suitable data processor(s) that, for example, can include a suitable microprocessor, digital signal processor (DSP), image processor, or the like, such as an integrated circuit (e.g., a field-programmable gate array).

The quadrature Doppler data is coupled to a color flow processor 30 which spatially processes the data into a two or three dimensional image format, in which the velocity values are color-coded. This Doppler color map is overlaid over the spatially corresponding B mode image by the display processor 36 to illustrate the locations in the anatomy where flow is taking place and qualitatively shows the velocity and direction of that flow by the color coding. Doppler data from a particular point in the image, selected by placement of a sample volume SV over that location in the image, is coupled to a spectral Doppler processor 32 which produces a spectral display of the variation and distribution of flow velocities at that point with time. The spectral Doppler display is forwarded to the display processor 36 for processing and display of the spectral Doppler display on the display screen 52.

For a stenosis exam workflow of the present invention, color flow data from the color flow processor 30 and, preferably, spatially corresponding B mode data from the B mode processor 24, is coupled to a color box position and steering angle processor 40. The color box position and steering angle processor controls the automation of settings and features of the color flow image, including properly positioning the color box, setting the Doppler angle of the Doppler beams, locating the sample volume SV in the image, and proper positioning of the flow angle cursor for Doppler angle correction. For control of the Doppler angle and acquiring data samples from a selected sample volume, the color box position and steering angle processor is coupled to the beamformer controller 16 to control the Doppler beam directions and timing. Setup and control of the color box position and steering angle processor is provided by the setting of controls on a user control panel 50. Graphical display of functions controlled by the color box position and steering angle processor, such as the outline of the color box, the sample volume graphic, and the flow angle cursor, is provided through a graphics processor 34 which is coupled to the display processor 36 to overlay the graphics over the ultrasound images. The operation of the color box position and steering angle processor 40 is more fully described in US patent application pub. no. 2014/0221838, entitled ULTRASOUND SYSTEM WITH AUTOMATED DOPPLER FLOW SETTINGS, which is incorporated by reference herein.

Figure 2:
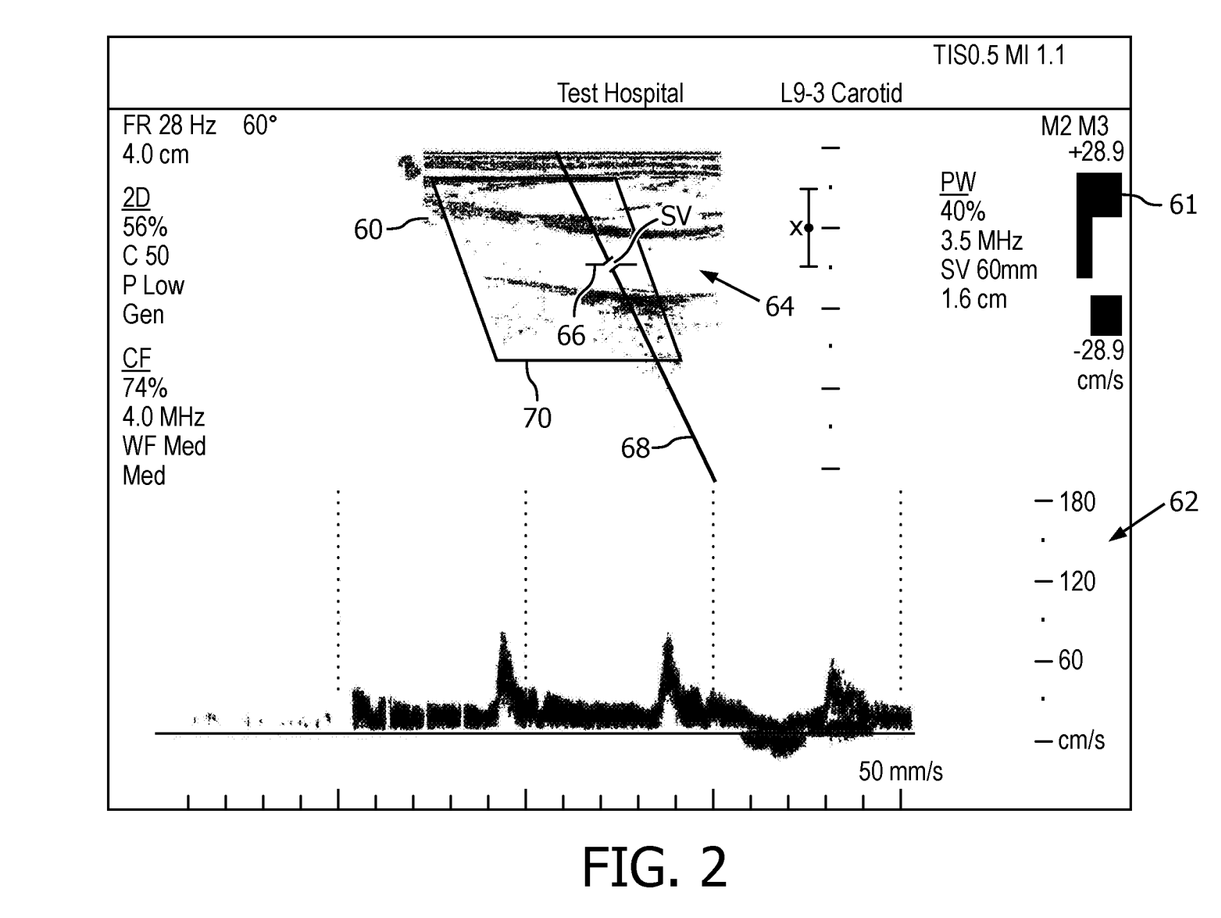
FIG. 2 illustrates an ultrasound display screen for a conventional ultrasound stenosis assessment exam.

FIG. 2 shows an ultrasound system display of a typical color flow/spectral Doppler duplex image 61 for conduct of a stenosis assessment exam. A two dimensional (2D) anatomical ultrasound image 60 is displayed at the top of the screen and a spectral Doppler display 62 is at the bottom of the screen, and is seen to have a vertical axis calibrated in velocity in cm/sec, and a horizontal axis calibrated in time in 50 mm/sec. Each vertical line of the spectral display illustrates the distribution of estimated velocities of the blood flow at that instant in time. Doppler interrogation is done inside the color box 70, and a color flow image is displayed inside this box. The surrounding portion of the image outside the color box 70 is shown in B mode grayscale without the color Doppler overlay. The use of a color box delineates the region where Doppler is to be performed, and repeated Doppler transmission for Doppler ensemble acquisition is not performed outside of the color box. Restricting the Doppler transmission to only the color box eliminates the need for repeated line interrogation outside the box and hence limits the total number of transmit-receive cycles needed to produce the image, thereby reducing the time needed to acquire the image which improves the real time frame rate of display. The Doppler beams for the spectral Doppler data are transmitted and received along the beam direction line 68 and the data samples used for the spectral Doppler display are acquired from echoes returning from the sample volume SV on the beam direction line. The Doppler flow direction cursor 66, used for angle correction, is aligned with the longitudinal orientation of the blood vessel 64 and is thus substantially parallel with the flow direction in the vessel, and the Doppler steering angle is the vertical angle of the color box 70 and the beam direction line 68, which are generally parallel to each other. In this example the Doppler steering angle is set to approximately a 60° angle with the longitudinal direction of the blood vessel 64.

Figure 3:
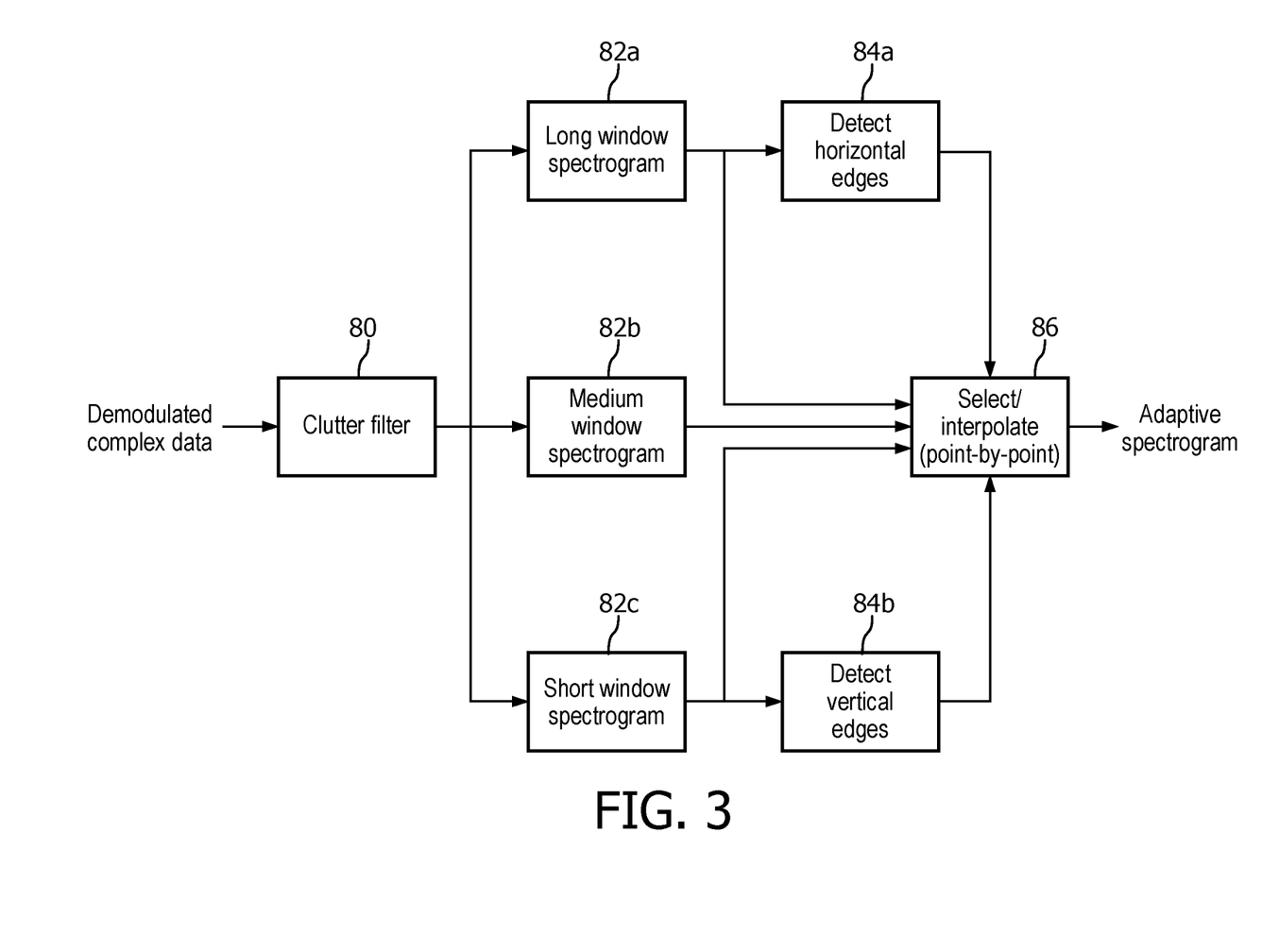
FIG. 3 illustrates in block diagram form an adaptive spectral Doppler processor using different FFT window lengths in accordance with the principles of the present invention.

FIG. 3 illustrates in block diagram form one implementation of the Doppler angle estimator and the spectral Doppler processor of FIG. 2 constructed in accordance with the principles of the present invention. The quadrature (I,Q) data samples acquired from the sample volume SV in the body and produced by the QBP filter 18 are coupled to a clutter or wall filter 80. When assessing blood flow velocities, the velocities of moving tissue or stationary anatomy in the body are unwanted and are, for the purposes of blood flow assessment, clutter. Since everything inside the color box 70 will be Doppler processed, the velocities of everything but blood flow are eliminated from further processing by the clutter filter or wall filter. This filter will block or discard all velocity estimates below a threshold level, generally one approaching a zero cm/sec velocity, from further processing, on the assumption that these velocities are produced from echoes returned from stationary or slowing moving tissue. Since these velocities are lower than the expected velocity range of blood flow, they are excluded from further Doppler processing and display by the clutter or wall filter 80.

In the illustrated implementation the complex data samples from the sample volume are applied to three spectrogram processors, a long window FFT processor 82a, a medium window FFT processor 82b, and a short window FFT processor 82c. Each of these processors execute an FFT (Fast Fourier Transform) algorithm which computes the discrete Fourier transform of a sequence of data samples to convert the samples from the time domain in which they were acquired to the frequency domain. Since the frequency domain values are proportional to the velocity of the blood flow which returned the signals the FFT processors thereby estimate the instantaneous velocity of blood flow as represented by the processed sample sequence. A typical FFT algorithm is of the form:

$$X_k = \sum_{n=0}^{N-1} x_n e^{-i2\pi k \frac{n}{N}} \quad k = 0, \ldots, N-1.$$

Where $x_n$ are the complex samples produced by the QBP filter. The complex data samples can be acquired one at a time in response to transmit pulses in the PW Doppler mode or by periodically sampling the echoes received in the CW Doppler mode. Typical data rates of the sample sequence (the transmit pulse repetition frequency, PRF) are 200 Hz to 2 kHz in the PW Doppler mode, while typical CW Doppler sample rates are 100-200 kHz. $X_k$ are the Doppler frequency-domain estimates in a range of −PRF/2 to +PRF/2. The variable n is a time index and k is a frequency index.

Each FFT processes a sequence of a different number of samples, referred to as a window length. In some embodiments, an ultrasound Doppler spectrogram display can use the log magnitude of the complex FFT results:

$Y_k = \log(|X_k|),$ or something substantially equivalent to compress a large dynamic range of power while discarding phase angle. The log-magnitude spectrograms with different window lengths can be resampled in horizontal (time) and vertical (Doppler frequency, velocity) dimensions to match the desired pixel spacing of the display and to facilitate adaptive combinations of multiple spectrograms. Resampling is a well-known technique, using for example polyphase finite impulse response (FIR) filters or spline interpolation.

In the FFT algorithm N is the number of samples in the window, typically 50-500 for PW Doppler and 1000-4000 for CW Doppler. Windows for successive executions of the FFT algorithm typically overlap in time so that the resultant Doppler spectral display is smooth and adequately sampled in time rather than appearing jagged and irregular. An exemplary overlap is 75%, for instance. The windowed data is generally extended with zeroes (zero padding) up to the next higher power of two for efficient FFT processing. In accordance with the principles of the present invention the three spectrogram processors 82a, 82b, and 82c have different window lengths, long, medium and short, respectively. Consequently exemplary window lengths of the three spectrogram processor would be 512 samples, 256 samples, and 64 samples, including zero padding. Another exemplary set of window lengths for the PW Doppler mode are 512 samples, 128 samples, and 64 samples.

Since the three spectrogram processors execute the FFT algorithm with different window lengths of data samples they will produce different results. The long window spectrogram processor 82*a* will produce frequency (velocity) estimates which are more precise in velocity but less precise in time. The short window spectrogram processor 82*c* will produce frequency estimates which are more accurate in time but less precise in velocity. Consequently the short window spectrogram processor would be preferred when the blood flow is rapidly changing, as it is during systole when the heart is quickly contracting or in the vicinity of a stenosis. The long window spectrogram processor would be preferred when the blood flow velocity is not changing rapidly, such as during diastole when the heart is relaxing or in a blood vessel which is not stenotic. It will be appreciated that multiple different spectrograms can be produced by time-multiplexing a single spectrogram processor with different window lengths.

Figure 4:
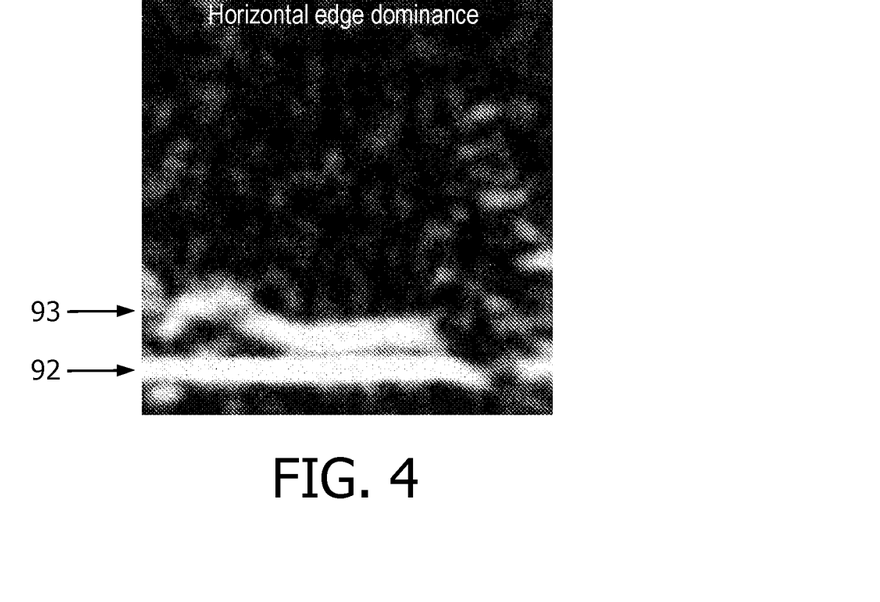
FIG. 4 illustrates detail of a spectral Doppler display when the velocity is changing slowly and the display is dominated by display segments with horizontal edges.

The exemplary implementation of FIG. 3 has a select/interpolate processor 86 which combines the estimates from the three spectrogram processors in a chosen way to produce a final spectrogram 62 for display. One way that the spectrograms can be combined is to interpolate the three velocities from the three spectrograms in time and velocity on a point-by-point basis. The final spectrogram produced by the select/interpolate processor will thus exhibit a range of velocities, each of which is interpolated from the corresponding velocities of the long, medium, and short window spectrograms. The select/interpolate processor is also seen to receive inputs from horizontal and vertical edge detectors 84*a* and 84*b*. The edge detectors can be coupled to the processor through programming interconnects (e.g. signal connections) within a section of a FPGA that implements horizontal and/or vertical edge detection for the received signals. The horizontal edge detector 84*a* detects the edges of spectral segments in the spectrograms produced by the long window spectrogram processor 82*a* and the vertical edge detector 84*b* detects the edges of spectral segments in the spectrograms produced by the short window spectrogram processor 82*c*. This is illustrated by the enlarged spectrogram segment images shown in FIGS. 4 and 5. FIG. 4 shows two horizontal spectral segments 92 and 93. The edges of these segments are detected by image processing which compares successive pixels in the image in vertical line directions and time across the image. When a horizontal segment is present, white pixels will be encountered when a vertical search finds one of these segments. As the pixel search continues vertically, successive pixels will exhibit a sharp transition from white to black at the edge of the segment. A comparison of the pixels will detect this significant transition and thus the edge of a horizontal segment. Searches along adjacent vertical lines will yield similar sharp transitions at or near the same vertical locus in the image, indicating the predominately horizontal orientation of the spectral segment. The horizontal edge detector 84*a* will signal the select/interpolate processor 86 that the spectrogram is extending predominately in a horizontal (time) direction.

Figure 5:
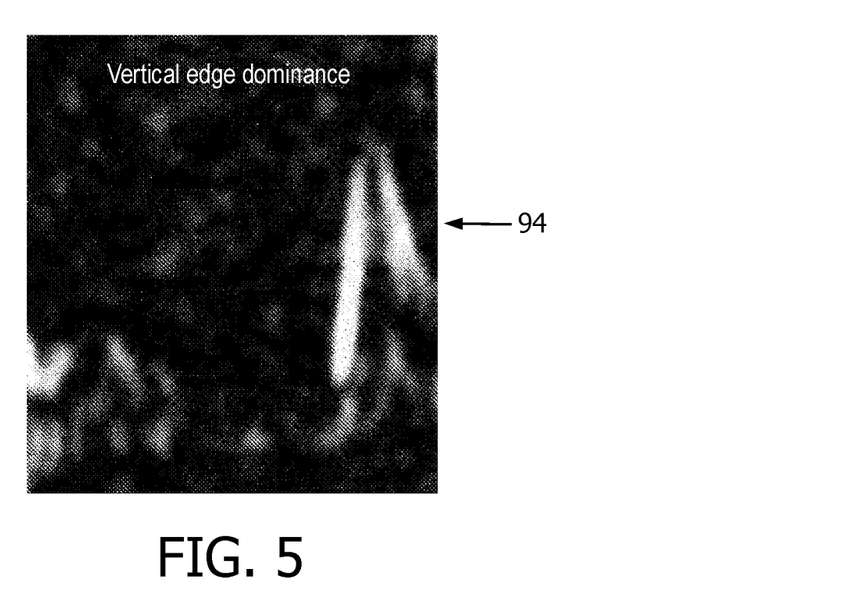
FIG. 5 illustrates detail of a spectral Doppler display when the velocity is changing rapidly and the display is dominated by display segments with more vertical edges.

Similarly, the vertical edge detector 84*b* compares successive pixels in a spectral image in horizontal line directions and velocity across the image, searching for edges of vertical spectral segments. Referring to FIG. 5, a spectrogram image with a vertical spectral segment is shown. When a vertical segment such as 94 is present, white pixels will be encountered when a horizontal search across the image finds one of these segments. As the pixel search continues horizontally, a comparison of successive pixels will exhibit a sharp transition from white to black at the edge of the segment. A comparison of the pixels will detect this significant transition and thus the edge of a vertical segment. Searches along adjacent horizontal lines will yield similar sharp transitions at or near the same horizontal locus in the image, indicating the predominately vertical orientation of the spectral segment 94. The vertical edge detector 84*b* will signal the select/interpolate processor 86 that the spectrogram is extending predominately in a vertical (velocity) direction. These pixel searches across an image are similar to those used for heart chamber border detection in an image as described in U.S. Pat. No. 6,491,636 (Chenal et al.), which is incorporated by reference herein. In a constructed embodiment the horizontal and vertical edge detectors comprise a two-dimensional spatial filter which detects edges in a two-dimensional array of pixel data.

The select/interpolate processor 86 responds to indication of a predominate direction of spectral segments at each horizontal (time) and vertical (velocity) pixel by choosing the corresponding window length spectrogram at that pixel for display as the final adaptive spectrogram. If the horizontal edge detector 84*a* signals a predominance of horizontal edges in its spectrogram, there is not much velocity variance or rapid velocity changes in the blood flow, and the select/interpolate processor will respond by using the spectrogram processed with the long window FFT as the final spectrogram for display, thereby accentuating velocity precision. When the vertical edge detector 84*b* signals a predominance of vertical edges in its spectrogram, there is a rapid velocity change presently underway in the blood flow, and the select/interpolate processor will respond by using the spectrogram processed with the short window FFT as the final spectrogram for display, thereby accentuating the rapid velocity change. If neither detector is dominant, the select/interpolate processor 86 can use the spectrogram produced by the medium window spectrogram processor 82*b*. Alternatively, the select/interpolate processor 86 may produce an interpolated final spectrogram from all three processors if no edge detector is dominant.

It will be understood that each block of the block diagram illustrations, and combinations of blocks in the block diagram illustrations, as well any portion of the systems and methods disclosed herein, can be implemented by computer program instructions. These program instructions may be provided to a processor to produce a machine, such that the instructions, which execute on the processor, create means for implementing the actions specified in the block diagram block or blocks or described for the systems and methods disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable hardware medium including, but not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computing device.

What is claimed is:

1. An ultrasonic diagnostic imaging system with a spectral Doppler display mode comprising:
- a source of complex echo data samples returned from a location of blood flow;
- a first spectrogram processor configured to execute a Fast Fourier Transform (FFT) algorithm using a long window of a first number of complex echo data samples and to produce a first spectrogram comprising first velocity estimates;
- a second spectrogram processor configured to execute an FFT algorithm using a short window of a second number of complex echo data samples and to produce a second spectrogram comprising second velocity estimates, wherein the first number of complex echo data samples is greater than the second number of complex echo data samples;
- a spectral display processor, adapted to use either the first or the second velocity estimates for production of an adaptive Doppler velocity spectrogram depending upon whether the velocity estimates are changing rapidly, during systole or in the vicinity of a stenosis, or slowly, during diastole or in a blood vessel which is not stenotic;
- a display, coupled to the spectral display processor, and adapted to display the adaptive Doppler velocity spectrogram;
- an interpolate processor is configured to be responsive to the first and second velocity estimates and configured to select velocity estimates of the spectrogram processors for display in the adaptive Doppler velocity spectrogram, wherein the interpolate processor selects velocity estimates from the first spectrogram processor in time periods when the blood flow velocity is changing slowly and velocity estimates from the second spectrogram processor in time periods when the blood flow velocity is changing rapidly; and
- an edge detector having inputs coupled to the first and second spectrogram processors and an output coupled to the interpolate processor,
  - wherein the interpolate processor is configured to produce the adaptive Doppler velocity spectrogram in response to the output of the edge detector
  - wherein the edge detector further comprises a horizontal edge detector having an input coupled to the first spectrogram processor and a vertical edge detector having an input coupled to the second spectrogram processor, and
  - wherein the interpolate processor is configured to be responsive to detection of a vertical spectral segment edge by the vertical edge detector to select a spectrogram produced by the second spectrogram processor as the adaptive velocity Doppler spectrogram.

2. An ultrasonic diagnostic imaging system with a spectral Doppler display, mode comprising:
- a source of complex echo data samples returned from a location of blood flow;
- a first spectrogram processor configured to execute a Fast Fourier Transform (FFT) algorithm using a long window of a first number of complex echo data samples and to produce a first spectrogram comprising first velocity estimates;
- a second spectrogram processor configured to execute an FFT algorithm using a short window of a second number of complex echo data samples and to produce a second spectrogram comprising second velocity estimates, wherein the first number of complex echo data samples is greater than the second number of complex echo data samples;
- a spectral display processor, adapted to use either the first or the second velocity estimates for production of an adaptive Doppler velocity spectrogram depending upon whether the velocity estimates are changing rapidly, during systole or in the vicinity of a stenosis, or slowly, during diastole or in a blood vessel which is not stenotic;
- a display, coupled to the spectral display processor, and adapted to display the adaptive Doppler velocity spectrogram;
- an interpolate processor is configured to be responsive to the first and second velocity estimates and configured to select velocity estimates of the spectrogram processors for display in the adaptive Doppler velocity spectrogram, wherein the interpolate processor selects velocity estimates from the first spectrogram processor in time periods when the blood flow velocity is changing slowly and velocity estimates from the second spectrogram processor in time periods when the blood flow velocity is changing rapidly; and
- an edge detector having inputs coupled to the first and second spectrogram processors and an output coupled to the interpolate processor,
  - wherein the interpolate processor is configured to produce the adaptive Doppler velocity spectrogram in response to the output of the edge detector,
  - wherein the edge detector further comprises a horizontal edge detector having an input coupled to the first spectrogram processor and a vertical edge detector having an input coupled to the second spectrogram processor, and
  - wherein the interpolate processor is responsive to detection of a horizontal spectral segment edge by the horizontal edge detector to select a spectrogram produced by the first spectrogram processor as the adaptive velocity Doppler spectrogram.

3. The ultrasonic diagnostic imaging system of claim 2, wherein the interpolate processor is further configured to produce the adaptive Doppler velocity spectrogram by interpolating spectrograms produced by the first and second spectrogram processors.

4. The ultrasonic diagnostic imaging system of claim 2, wherein the interpolate processor is configured to be responsive to detection of a vertical spectral segment edge by the vertical edge detector to select a spectrogram produced by the second spectrogram processor as the adaptive velocity Doppler spectrogram.

5. The ultrasonic diagnostic imaging system of claim 2, wherein the complex echo data samples further comprise complex echo data samples acquired in a continuous wave (CW) Doppler mode.

6. The ultrasonic diagnostic imaging system of claim 2, wherein the complex echo data samples further comprise complex echo data samples acquired in a pulsed wave (PW) Doppler mode.

7. The ultrasonic diagnostic imaging system of claim 6, wherein the complex echo data samples further comprise a sequence of time-sequential complex echo data samples.

8. The ultrasonic diagnostic imaging system of claim 2, further comprising a third spectrogram processor configured to execute an FFT algorithm using a window of a third number of complex echo data samples and to produce third velocity estimates, wherein the first number is greater than the second number and the second number is greater than the third number.

9. The ultrasonic diagnostic imaging system of claim 8, wherein the interpolate processor is configured to use the third velocity estimates to produce the adaptive velocity spectrogram when blood flow velocity is changing at a rate which is not predominately rapid, in comparison to diastole, and not predominately exhibiting not much velocity variance.

10. The ultrasonic diagnostic imaging system of claim 8, wherein the interpolate processor is configured to use the first velocity estimates to produce the adaptive velocity spectrogram when blood flow velocity is changing relatively slowly in comparison to systole.

11. The ultrasonic diagnostic imaging system of claim 10, wherein the interpolate processor is configured to use the first velocity estimates produced in response to detection of a horizontal spectral segment edge.

12. The ultrasonic diagnostic imaging system of claim 8, wherein the interpolate processor is configured to use the second velocity estimates to produce the adaptive velocity spectrogram when blood flow velocity is changing relatively rapidly in comparison to diastole.

13. The ultrasonic diagnostic imaging system of claim 12, wherein the interpolate processor is configured to use the second velocity estimates produced in response to detection of a vertical spectral segment edge.

* * * * *